United States Patent [19]

Ogawa et al.

[11] 4,062,936

[45] Dec. 13, 1977

[54] CARRIER FOR IMMUNOCHEMICAL MEASUREMENT

[75] Inventors: Nobuhisa Ogawa, Omiya; Masakatsu Hashimoto, Tokyo, both of Japan

[73] Assignee: Mochida Seiyaku Kabushiki Kaisha, Tokyo, Japan

[21] Appl. No.: 628,344

[22] Filed: Nov. 3, 1975

[30] Foreign Application Priority Data

Nov. 16, 1974 Japan ................................ 49-132175

[51] Int. Cl.$^2$ ...................... G01N 33/16; G01N 31/02
[52] U.S. Cl. .................................... 424/12; 23/230 B; 252/408
[58] Field of Search ...................... 23/230 B; 252/408; 424/3, 11, 12; 260/112 B

[56] References Cited

U.S. PATENT DOCUMENTS

| 3,574,137 | 4/1971 | Decasperis ..................... 23/230 B X |
| 3,607,783 | 9/1971 | Tata et al. ....................... 23/230 B X |
| 3,715,427 | 2/1973 | Hirata ............................... 424/12 X |

FOREIGN PATENT DOCUMENTS 1,210,819  4/1970  United Kingdom ............... 23/230 B

OTHER PUBLICATIONS

*Gradwohl's Clinical Laboratory Methods & Diagnosis,* vol. 2, Mosby & Co., St. Louis (1970), pp. 1559–1560.

*Primary Examiner*—Sidney Marantz
*Attorney, Agent, or Firm*—Brisebois & Kruger

[57] ABSTRACT

Carrier for immunochemical measurement wherein tannic acid is bound to blood cells in the proportion of 30 to 500 mg per milliliter of the blood cells.

14 Claims, No Drawings ic measurement is usually prepared from blood cells obtained from various animals without any chemical treatment or blood cells first treated with an appropriate fixing agent such as formaldehyde, pyruvinaldehyde, hydrogen peroxide, or the like, and then treated with a binding agent such as tannic acid, bisdiazobenzidine, 1,3-difluoro-4,6-dinitrobenzene or the like.

CARRIER FOR IMMUNOCHEMICAL MEASUREMENT

BACKGROUND OF THE INVENTION

In recent years, the measurement of biologically active components in a living body, such as insulin, growth hormones, prolactin, gastrin, adrenocorticotrophic hormones, thyroid hormones, angiotensin, and the like, has been recognized as having important significance in the diagnosis, therapy, and prevention of human diseases or in various functional tests. As a result, such measurements have recently come to be carried out very frequently.

However, as all these biological components are present in very small quantities, they cannot be measured by a conventional chemical method and are measured by an immunochemical method, such as by a radioimmunoassay (hereinafter referred to as RIA) which enables extraordinarily highly sensitive measurement.

However, the RIA method is unsuitable for measuring components of the human body as a matter of daily routine in general medical institutions, since it requires special instruments utilizing isotopes and the operation thereof is complicated and inconvenient.

Heretofore, a well known simple method for measuring biological components of the human body has comprised sensitizing a carrier composed of blood cells, polystyrene latex, kaolinite, bentonite, active charcoal, crystalline cholesterin, and the like with an antigen or antibody, and then reacting the carrier with the antibody or antigen present in the sample and causing an immunochemical agglutination reaction or an agglutination inhibition reaction. Particularly, a method using blood cells as the carrier is much preferred because of its high sensitivity.

The blood cell used as a carrier for the abovementioned immunochemical measurement is usually prepared from blood cells obtained from various animals without any chemical treatment or blood cells first treated with an appropriate fixing agent such as formaldehyde, pyruvinaldehyde, hydrogen peroxide, or the like, and then treated with a binding agent such as tannic acid, bisdiazobenzidine, 1,3-difluoro-4,6-dinitrobenzene or the like.

The animals from which the blood cell is obtained are generally mammals, e.g. cattle, horses, sheep, rabbits, humans, etc. or birds, e.g. chicken, pigeons, turkeys, etc., though other animals including reptiles such as crocodiles and snakes and amphibians such as frogs, etc., and marine animals such as dolphins may also be used.

Although the blood cell obtained from these animals can be used in its untreated state, in most cases, a fixed blood cell, treated with the above mentioned fixing agent is used because an untreated blood cell has poor strength in its natural form tending to hemolyze during mechanical or chemical treatments.

The term "blood cells" in this specification means the material component in the blood consisting mainly of red blood cells which includes untreated blood cells without any treatment and the said fixed blood cells. The quantity of blood cells is represented by the apparent volume of blood cells obtained by the centrifugation of blood.

These blood cells have to be treated with the binding agent as mentioned above before they are used as a carrier. It is hard to bind antigens or antibodies to blood cells which are not treated with the binding agent and even if they are bound, no uniform product can be obtained, resulting in failure to obtain a carrier having a stable sensitivity. On the other hand, a blood cell treated with a binding agent exhibits improved bonding power on the surface of the blood cell enhancing the binding to the antigen or antibody, so that a carrier with a better immunochemical agglutination reaction or agglutination inhibition reaction is obtained. For instance, when tannic acid is used as a binding agent according to the conventional method, a suspension of blood cells in a buffer solution (blood cell concentration 2 to 8%) is mixed with an equal volume of a solution of binding agent in the said buffer solution and both components are allowed to react at 37° to 56° C for 30 to 60 minutes. The said solution of tannic acid is usually a concentration of 1/20,000 to 1/40,000, the representation 1/20,000 of said tannic acid solution indicates that the 20,000 ml solution was prepared by adding 1g of the solute to the solvent. Other cases follow suit.

As above, if blood cells are treated with tannic acid, about 0.3 to 2.5 mg of tannic acid is bound to 1 ml of blood cells. The blood cells have a sensitivity of about 100 ng/ml in the measurement of human serum albumin (hereinafter referred to as HSA) with the blood cells as a carrier. This value of sensitivity is comparatively high as compared with that with other types of carriers, such as the fine particles of polystyrene latex, other than the blood cells. Nevertheless, the value is no more than 1/10 to 1/10,000 as compared with the sensitivity of the RIA method.

Accordingly, in immunochemical agglutination reactions or agglutination inhibition reactions, it is impossible to obtain a sensitivity comparable to that of a RIA method by using a conventional carrier. In other words, the measurement of such high sensitivity required a novel carrier.

As a highly sensitive and highly specific carrier used for an immunochemical measurement the carrier should have the following properties: when the carrier is sensitized with an antigen or antibody corresponding to the object substance of the measurement, any slight quantity of antigen or antibody present in a living body as biological components can readily bring about an immunochemical reaction with the antibody or antigen with which the carrier was sensitized and, based on this reaction, the sensitized carrier undergoes a complete agglutination reaction; however, in the event that the immunochemical reaction does not take place, no spontaneous agglutination occurs.

BRIEF SUMMARY OF THE INVENTION

The object of the present invention is to provide a carrier which, in a simplified measurement of biological components based on the utilization of an immunochemical agglutination reaction or an agglutination inhibition reaction, gives a high sensitivity and specificity comparable to that of Radio-immunoassay.

DETAILED DESCRIPTION OF THE INVENTION

The present invention relates to a carrier for immunochemical measurement characterized in that tannic acid is bound to blood cells in a proportion of 30 to 500 mg per 1 ml of blood cells. Heretofore, the qualitative and quantitative measurements of the biological components of a living body have been carried out by utilizing immunochemical reactions. Although these methods were quite simple as compared with radioimmunoassay (RIA method), they have drawbacks in that an antigen-antibody reaction has produced a low sensitivity and specificity as compared with the said RIA method because no one could find a suitable carrier for carrying antigen and antibody which reacts with biological components through an immunochemical reaction.

As a consequence of the investigation by the present inventors, it was found, by mixing the blood cells with a large quantity of tannic acid, that a carrier consisting of blood cells in which 30 to 500 mg of tannic acid is bound to 1 ml of blood cells, shows extremely superior properties in immunochemical measurements.

The carrier of the present invention is usually prepared by mixing and reacting a blood cell suspension containing 2 to 4% blood cells in a buffer solution with a solution of tannic acid in the said buffer solution at a concentration of 1/50 to 1/1,000 tannic acid, so that 30 to 500 mg of tannic acid is bound to 1 ml of the blood cells.

The blood cells used in the present invention may be of any type which has been used as a carrier for conventional immunochemical measurements.

The quantity of tannic acid to be bound to blood cells is preferably in the range of 30 to 500 mg per 1 ml of the blood cells. If the quantity is less than 30 mg, the carrier cannot achieve the desired high sensitivity and specificity. If it exceeds 500 mg, the carrier has too intense an agglutination property to be controlled by the method hereinafter described, and therefore the carrier can no longer be used in an immunochemical measurement.

Usually, in the reaction between blood cells and tannic acid, equal quantities of blood cell suspension containing 2 to 4% blood cells and a tannic acid solution having a concentration of 1/50 to 1/1,000 are mixed; however, the concentration of blood cells in the suspension, the concentration of tannic acid in the tannic acid solution and the mixing ratio of the blood cell suspension and the tannic acid solution are made so that the quantity of tannic acid bound to 1 ml of blood cells may be in the range of 30 to 500 mg. That is to say, this is done either by suspending blood cells in a tannic acid solution of 1/100 to 1/2,000 concentration or by adding tannic acid itself to a blood cell suspension of 1 to 2% concentration.

The buffer solution to suspend blood cells and dissolve tannic acid may be any type of buffer solution conventionally used in an immunochemical reaction, and moreover, a physiological saline solution can be used, preferably a phosphate-buffer saline solution.

Although the blood cells may be reacted with tannic acid at room temperature, better results are obtained by heating at a temperature ranging from 37° to 56° C, which is the usual temperature range adopted in general immunochemical processes.

As a result of the present carrier retaining a larger quantity of tannic acid than the conventional carriers, the agglutination property of the carrier itself is much enhanced and at the same time, it can bind a larger quantity of antigen or antibody to itself than the conventional carriers.

The relation between the quantity of tannic acid which has been added for treating blood cells and the quantity of tannic acid bound to the blood cells is shown in Table 1.

TABLE 1

| Quantity of tannic acid added to 1 ml of blood cells (mg) | Tannic acid bound to 1 ml of blood cells (mg) | Rate of Binding (%) |
| --- | --- | --- |
| 1 | 0.94 | 94.0 |
| 10 | 8.82 | 88.2 |
| 100 | 86.2 | 86.2 |
| 600 | 498 | 83.0 |

The values shown in Table 1 are those of tannic acid measured with Folin-Denis reagent in ethanol extracts from the blood cells treated with tannic acid. About the same values are also obtained by measuring the residual tannic acid content in the supernatant after the blood cells are bound with tannic acid and deducing it from the initial quantity of tannic acid. From this table, a majority of the added tannic acid is found to be bound to blood cells regardless of the quantity of tannic acid added to blood cells.

Next, studies have been made on the agglutination property of the carrier itself, the agglutination property when bovine serum albumin is added as the stabilizer for a reaction system, and the agglutination property of a carrier sensitized with anti-HSA antibody to compare the conventional carriers with the present carrier. The agglutination property of a carrier itself generally varies with pH and ionic strength, etc., of the buffer solution in which the carrier is suspended. In the present example, carriers bound with various quantities of tannic acid are suspended in a phosphate buffer saline solution (pH 6.4 and concentration 0.076 Mol) at a concentration of 0.133%, and 0.5 ml of each suspension is placed in a small test tube and allowed to stand for two hours, after which the agglutination property of the carrier is evaluated on the basis of the sedimentation patterns at the bottom of the tube.

The agglutination property of a carrier itself, with the addition of bovine serum albumin as a stabilizer for a reaction system, is measured in the same manner as in the absence of the serum albumin, except that a phosphate-buffer saline solution containing 0.2% bovine serum albumin is used for suspending the carrier. The agglutination property of a carrier sensitized with an anti-HSA antibody is measured in the same manner as in Column 2 of Table 2, except that the carrier sensitized with the anti-HSA antibody is used. The criteria for sedimentation patterns at the bottom of a test tube are set according to the following:

+++    Very intense positive reaction
++    Intense positive reaction
+    Positive reaction
−    Negative reaction The results are summarized in Table 2.

TABLE 2

| | Column 1 | Column 2 | Column 3 |
| --- | --- | --- | --- |
| Tannic acid bound to 1 ml of blood cells (mg) | Agglutination property of carrier itself | Agglutination property of carrier itself with the addition of bovine serum albumin as a stabilizer for reaction system | Agglutination property of carrier sensitized with an anti-HSA antibody |
| 500 | +++ | ++ | − |
| 100 | +++ | + | − |
| 10 | ++ | − | − |
| 1 | − | − | − |

Table 2 shows that the carrier of the present invention bound with a large quantity of tannic acid brings about a spontaneous agglutination reaction, while the conventional carriers bound with only a small quantity of tannic acid do not. This suggests that the bonding of blood cells with a large quantity of tannic acid leads to occurrence of a certain change on the surface of blood cells which brings about an increase in the agglutination property of the carrier itself.

The relation between the quantity of tannic acid bound to blood cells and the quantity of antibody or antigen bound to the carrier which combines with tannic acid was also studied.

The quantity of antibody or antigen bound to a carrier is measured through determination of the quantity of antibody or antigen remaining in the supernatant after the sensitization of the carrier with antibody or antigen by an immunological diffusion method, and deducing it from the initial quantity of antibody or antigen added for the purpose of sensitization.

In the present example, a rabbit gamma globulin and HSA are respectively used as antibody and antigen.

The results are summarized in Table 3.

TABLE 3

| Tannic acid bound to 1 ml of blood cells (mg) | bound antibody (gamma globulin) (mg) (5mg addition to 0.2 ml blood cells) | Bound antigen (HSA) (mg) (2mg adition to 0.2 ml blood cells) |
|---|---|---|
| 500 | 3.0 (60%) | 1.7 (85%) |
| 100 | 2.5 (50%) | 2.5 (75%) |
| 50 | 1.9 (38%) | 1.3 (65%) |
| 10 | 0.6 (12%) | 0.7 (35%) |
| 1 | 0.4 ( 8%) | 0.3 (15%) |

As is obvious from Table 3, the more bound tannic acid a carrier has, the more gamma globulin it has to be bound to said carrier, and a carrier bound with 500 mg tannic acid per 1 ml of blood cells binds about 7.5 times as much gamma globulin as that bound with 1 mg tannic acid. The situation is similar in the case of the quantity of bound antigen. In conclusion, the carrier of the present invention has a remarkably increased potency to bind antibody or antigen as compared with the conventional carriers.

In addition, the carrier of the present invention has the advantage that the high agglutination property and potency to bind a large quantity of antigen or antibody can be controlled in accordance with the purpose of application. Such control is most effectively made in applying the known art most advantageously, e.g., in the sensitization of a carrier with antigen or antibody so as to control the quantity of antigen or antibody, the addition of normal rabbit albumin, bovine serum albumin or a surfactant etc. as stabilizer for the immunochemical reaction system, the control of pH and ionic strength of the immunochemical reaction system, or the combination of this well known art. (See Table 2)

The carrier of the present invention can be used as a carrier for antigen or antibody in the immunochemical agglutination and agglutination inhibition reactions. For instance, when HSA is measured by using the present carrier, the measurement of 100 pg/ml order of HSA is possible. That is to say, the sensitivity of the measurement is enhanced about 1,000 times as compared with the use of conventional carriers.

The following Experiments and Examples will concretely illustrate the present invention.

EXPERIMENT 1

2 ml of sheep blood cells fixed with formalin was suspended in 60 ml of phosphate-buffer saline solution. The suspension was mixed with 60 ml of a solution of tannic acid of varied concentrations dissolved in the said buffer solution, and the mixture was reacted at 56° C for 30 minutes. Thus, several carriers with the varied bound quantities of tannic acid were obtained. Each of the carriers was suspended in 60 ml of the said buffer solution and was then mixed with antibody solution prepared by dissolving 60 mg of an anti-HSA antibody (as rabbit gamma globulin) into the said buffer solution. The mixture was reacted at 56° C for 30 minutes until the carrier was sensitized with the anti-HSA antibody. Thereafter each of the sensitized carriers thus obtained was washed with 50 ml of buffer solution, and prepared into a 1% suspension in a phosphate buffer saline solution containing 10% of sucrose, 0.1% of bovine serum albumin and 0.02% of normal rabbit serum.

0.1 ml of each of the sensitized carrier suspensions was placed in a test tube of an inner diameter of about 9mm having a hemispherical bottom and mixed gradually with 0.3 ml of the phosphate buffer saline solution to give a 0.25% suspension, followed by the additions of 0.1 ml of HSA solutions respectively with 0.05, 0.1, 0.2, 0.5, 1.0, 2.0, 5.0 10, 20, 50 or 100 ng/ml of HSA. After shaking, the mixtures were allowed to stand for 2 hours. The sedimentation patterns developed at the bottom of the test tubes were observed, and the results were judged as negative and positive respectively according to whether a sedimentation ring was formed or not.

Table 4 illustrates the results of sensitivities of various carriers exhibited in the HSA measurements as represented in terms of the minimum quantities of HSA necessary for giving positive reactions.

TABLE 4

| Concentration of tannic acid solution used for treating blood cells | Tannic acid bound to 1 ml of blood cells (mg) | Sensitivity in HSA measurement (ng/ml) |
|---|---|---|
| 1/50 | 500 *(498) | 0.5 |
| 1/250 | 100 (103) | 0.1 |
| 1/900 | 30 (29) | 5.0 |
| 1/2,500 | 10 (10.4) | 20 |
| 1/30,000 | 1 (0.96) | 100 |

*The parenthesized figures are actually measured values.

As evident from Table 4, the best result was obtained with the carrier wherein 100 mg of tannic acid is bound to 1 ml of blood cells. This carrier exhibited about 1,000 times as great sensitivity as the conventional one wherein only 1 mg of tannic acid is bound to 1 ml of blood cells.

EXPERIMENT 2

60 ml of each of the carrier suspensions prepared in the same manner as in Experiment 1 was mixed with a solution of 6 mg of 2,4-dinitrophenol-bovine serum albumin combination product (hereinafter referred to as DNP-BSA) in 60 ml of phosphate buffer saline solution, and the solution was reacted at 56° C for 30 minutes until the carrier was sensitized with DNP-BSA. Then each of the carriers was washed with 50 ml of the above-mentioned buffer solution and prepared into 1% suspension in the phosphate buffer saline solution containing 10% of sucrose, 0.1% of bovine serum albumin and 0.02% of normal rabbit serum.

With the sensitized carriers, the maximum dilution ratio of anti-serum necessary for the occurrence of an agglutination reaction of the carriers was studied first.

An anti-DNP-BSA anti-serum was prepared by mixing Freund's Complete Adjuvant with DNP-BSA by a conventional method and thereby immunizing rabbits. The absorption of the serum with BSA yielded an anti-serum which exhibited an antibody activity only to DNP. The anti-serum was diluted with 0.25% saline solution containing 1% BSA in the order of 1, 10, 20, 50, 100, 200, 300, 400, and 500 times. Then, 0.1 ml of the diluted serums was added to a test tube which contained 0.1 ml of each of the said sensitized carrier suspensions and 0.3 ml of phosphate buffer saline solution and shaken. After allowing to stand for 2 hours, the maximum dilution ratio of anti-serum necessary for the occurrence of an agglutination reaction of the carriers was determined.

Next, some agglutination inhibition systems were composed between each of the sensitized carriers and the anti-serum determined at the maximum dilution ratio necessary for the agglutination reaction. Each of the systems thus obtained was investigated for its sensitivity in the DNP measurement.

For each of the agglutination inhibition reaction systems, 0.1 ml of the said anti-serum of maximum dilution was mixed in a test tube with 0.1 ml of a DNP solution containing 50, 100, 200, 300, 500, 700 or 1,000 ng/ml of DNP in phosphate buffer saline solution, to which were added 0.1 ml of said sensitized carrier suspension and 0.2 ml of phosphate buffer saline solution. After shaking and allowing to stand for 2 hours, the sedimentation pattern developed on the bottom of the test tube was observed. In the case of a sedimentation ring being formed, the result was judged as positive, while it was judged as negative when a sedimentation ring was not formed.

The sensitivities of the carriers are summarized in Table 5, being represented in terms of the minimum quantities of DNP necessary for the occurrence of positive reactions.

TABLE 5

| Concentration of tannic acid solution used for treating blood cell | Tannic acid bound to 1 ml of blood cell (mg) | Maximum ratio of dilution of anti-serum necessaray for the occurrence of agglutination reaction | Sensitivity in the DNP measurement (ng/ml) |
| --- | --- | --- | --- |
| 1/50 | 500 | 300 | 100 |
| 1/250 | 100 | 300 | 100 |
| 1/900 | 30 | 100 | 200 |
| 1/2,500 | 10 | 50 | 1,000 |
| 1/30,000 | 1 | * | — |

*No agglutination occurs even when the undiluted serum is used.

As shown in Table 5, although the conventional carriers bound with 1 mg tannic acid per 1 ml of blood cell cannot be agglutinated even when the undiluted antiserum is used, the carrier of the present invention bound with 100 mg tannic acid per 1 ml of blood cell can bring about an agglutination reaction with the anti-serum diluted three hundred fold.

The carrier of the present invention exhibited 5 to 10 times higher sensitivity in the measurement than the conventional carriers.

It is known from these experiments that the use of the carrier of the present invention in an immunochemical agglutination inhibition reaction enables the realization of a high magnification of dilution of anti-serum as compared with the case of conventional carriers, and therefore measurement of higher sensitivity is possible enabling the use of anti-serums of low antibody titer which have hitherto been impossible.

EXAMPLE 1

30 ml of sheep blood cells fixed with formaline was washed with 300 ml of phosphate buffer saline solution and then suspended into the buffer solution making the total volume of the solution 900 ml. To the suspension was added 900 ml of a tannic acid solution of 1/300 concentration dissolved in the said buffer solution, and the mixture was reacted at 56° C for 30 minutes. After the reaction, the carrier was twice washed with 600 ml of the buffer solution each time. The carrier in this example has about 90 mg of tannic acid per 1 ml of blood cells bound to itself.

EXAMPLE 2

50 ml of chicken blood cells fixed with pyruvinaldehyde was washed with ten times the physiological salt solution and then again suspended into 1,000 ml of the said solvent.

The said blood cell suspension was mixed with 2,000 ml of a tannic acid solution of 1/350 concentration and the mixture was reacted at 25° C for 60 minutes. After the reaction the carrier was washed with 1,000 ml of the said solvent. The carrier in this Example was bound with about 100 mg of tannic acid per 1 ml of blood cells.

EXAMPLE 3

50 ml of rabbit blood cells fixed after treatment with hydrogen peroxide was washed with 500 ml of borate buffer saline solution and then again suspended into the said buffer solution. The suspension was mixed with 1,500 ml of tannic acid solution of 1/500 concentration dissolved in the said buffer solution, and the mixture was reacted at 56° C for 45 minutes. After the reaction, the product was washed with 1,000 ml of the said buffer solution to give a carrier. The carrier in this Example takes about 50 mg of tannic acid per 1 ml of blood cell.

EXAMPLE 4

30 ml of untreated bovine blood cells was washed with 500 ml of veronal buffer solution, after which the blood cells were centrifuged. The blood cells were suspended into a tannic acid solution prepared by dissolving 1 g of tannic acid into 1,000 ml of the said buffer solution, and the suspension was reacted at 37° C for 30 minutes. After the reaction, the product was washed with the said buffer solution to give a carrier.

The carrier in this Example has about 30 mg of tannic acid per 1 ml of blood cells.

EXAMPLE 5

20 ml of bovine blood cells fixed with hydrogen peroxide was washed with 300 ml of phosphate buffer saline solution and then suspended into the said buffer solution making the total volume of the solution 600 ml.

The said blood suspension was mixed with a solution of tannic acid 1/50 concentration dissolved in the said buffer solution, and the mixture was reacted at 56° C for 30 minutes. After the reaction, the product was washed with the said buffer solution to give a carrier. The carrier in this Example contains about 500 mg of tannic acid per 1 ml of blood cells.

As mentioned above, the carrier of the present invention for immunochemical measurements has a higher sensitivity and higher specificity as compared with conventional carriers so that it easily brings about an immunochemical reaction even when the quantity of biological components is very small, and based on this reaction, it shows a complete agglutination reaction. Therefore, the use of the carrier of the present invention facilitates the measurement of biological components affording itself a very high medical value.

What is claimed is:

1. A reaction system for immunochemical measurement comprising a carrier containing blood cells which are bound to tannic acid in a quantity of 30 to 500 mg of tannic acid per 1 ml of the blood cells, said carrier being sensitized with an antigen or antibody.

2. A reaction system for immunochemical measurement according to claim 1, wherein the blood cells are obtained from at least one animal in an untreated state.

3. A reaction system for immunochemical measurement according to claim 1 which has additionally been adapted in accordance with the purpose of measurement by adding a stabilizer.

4. A reaction system for immunochemical measurement according to claim 1 which has additionally been adapted in accordance with the purpose of measurement by controlling its pH.

5. A reaction system for immunochemical measurement according to claim 1 which has additionally been adapted in accordance with the purpose of measurement by controlling its ionic strength.

6. A method for measuring immunochemical biological components which comprises the step of bringing the reaction system of claim 1 into an immunochemical agglutination or agglutination inhibition reaction with a test sample containing the biological components to be measured.

7. A carrier for immunochemical measurement according to claim 1, wherein blood cells are obtained from at least one animal and fixed with an appropriate fixing agent.

8. A carrier according to claim 7 wherein the appropriate fixing agent is selected from the group consisting of formaldehyde, pyruvicaldehyde and hydrogen peroxide.

9. A process for preparing a reaction system for immunochemical measurement comprising blood cells which are bound to tannic acid in the proportion of 30 to 500 mg of tanic acid per 1 ml of the blood cells and an antigen or antibody, which process comprises the steps of reacting a blood cell suspension prepared by suspending blood cells in a buffer solution with a tannic acid solution, the concentrations and mixing ratio of said solutions being such as to bind 30 to 500 mg of tannic acid to 1 ml of blood cell to provide a carrier, and then sensitizing said carrier with an antigen or antibody.

10. A process according to claim 9, wherein a blood cell suspension with a blood cell concentration of 2 to 4% in a buffer solution is mixed and reacted with a solution containing tannic acid dissolved in the same buffer solution at a concentration of 1/50 to 1/1,000 so that 30 to 500 mg of tannic acid is bound to 1 ml of blood cells.

11. A process according to claim 9, wherein the blood cells to be used are selected from the group consisting of natural blood cells obtained from animals and fixed blood cells obtained by fixing natural blood cells with a fixing agent.

12. A process according to claim 9, wherein said reaction temperature is in the range of 37° to 56° C.

13. A process for preparing a reaction system for immunochemical measurement comprising blood cells which are bound to tannic acid in a proportion of 30 to 500 mg of tannic acid per 1 ml of the blood cells, which process comprises the steps of reacting blood cells and tannic acid in a buffer solution so that 30 to 500 mg of tannic acid is bound to each ml of blood cells to form a carrier and then sensitizing said carrier with an antigen or antibody.

14. A process according to claim 13, wherein the buffer solution is selected from the group consisting of phosphate buffer saline solution, physiological salt solution, borate buffer saline solution, or veronal buffer solution.

* * * * *